United States Patent [19]

Imai et al.

[11] 4,319,883
[45] Mar. 16, 1982

[54] METHOD FOR DETERMINING CATECHOLIC COMPOUNDS AND THEIR RELATED COMPOUNDS

[75] Inventors: Kazuhiro Imai; Shigemitsu Yamada, both of Tokyo; Hidehiro Kubota, Kawasaki; Jun Sakamaki, Kasukabe, all of Japan

[73] Assignee: ATTO Corporation, Tokyo, Japan

[21] Appl. No.: 133,977

[22] Filed: Mar. 26, 1980

[30] Foreign Application Priority Data

Mar. 30, 1979 [JP] Japan ................................ 54-36911

[51] Int. Cl.³ ...................... G01N 33/52; G01N 21/25
[52] U.S. Cl. ............................... 23/230 B; 23/230 R; 23/932
[58] Field of Search ................ 424/7; 23/932, 230 B, 23/230 R

[56] References Cited

U.S. PATENT DOCUMENTS

| | | | |
|---|---|---|---|
| 2,902,348 | 9/1959 | Ostrander | 23/230 R |
| 2,981,606 | 4/1961 | Keston | 23/932 X |
| 3,653,841 | 4/1972 | Klein | 23/932 X |
| 3,886,045 | 5/1975 | Meiattini | 435/28 X |
| 4,166,719 | 9/1979 | Renton | 23/230 R |

FOREIGN PATENT DOCUMENTS

| | | | |
|---|---|---|---|
| 17174 | 10/1980 | European Pat. Off. | 23/932 |
| 545926 | 3/1977 | U.S.S.R. | 23/230 B |
| 550568 | 3/1977 | U.S.S.R. | 23/230 M |

OTHER PUBLICATIONS

*Nature;* MacMillan Journals Limited; 170:249-250; 8/1952.
Chem. Abstracts, 80:149349e; 1974.
Gradwohl's Clinical Laboratory Methods and Diagnosis, vol. 1, 7th Ed., The C. V. Mosby Co., Saint Louis; 1970; pp. 279-281.
Chemical Abstracts 79:100290u; 1973; Spectrophotometric Determination of Pyrocatechol.
Shriker, R. L.; Organic Compounds; 3rd Ed.; John Wiley & Sons, Inc., New York; 1948; pp. 98-99.

*Primary Examiner*—Kenneth M. Schor
*Attorney, Agent, or Firm*—Brumbaugh, Graves, Donohue & Raymond

[57] ABSTRACT

Disclosed are a method and an apparatus for determining catecholic compounds and their related compounds contained in a substance by utilizing the specific reactivity of the compounds with ferric chloride and potassium ferricyanide as reaction reagents. The reaction products are analyzed by spectrophotometry, preferably in combination with high-performance liquid chromatography, so as to determine catecholic compounds and their related compounds.

3 Claims, 8 Drawing Figures

METHOD FOR DETERMINING CATECHOLIC COMPOUNDS AND THEIR RELATED COMPOUNDS

BACKGROUND OF THE INVENTION

This invention relates to a new method for determining catecholic compounds and their related compounds and an apparatus for the determination thereof by this method.

Catecholic compounds are found in the animal and vegetable kingdoms, and among them, catecholamines, which play an important role among mammals, may be cited as typical. It is of utmost importance, therefore, in the fields of medicine, pharmacy, biochemistry, pharmacology, neurochemistry, etc. to determine the fluctuation in a biological substance in the amount of catecholamines (such as dopamine, norepinephrine or epinephrin) and their related compounds or their metabolites (3-methoxytyramine, normetanephrine, metanephrine, homovanillic acid, vanillylmandelic acid, 3,4-dihydroxyphenylacetic acid, 3,4-dihydroxymandelic acid, 3-methoxy-4-hydroxyphenylglycol, 3,4-dihydroxyphenylglycol, etc.).

While catecholamines and their metabolites are present in very small quantities, various methods for the determination of catecholamines have recently been put into practical use. The methods applied are selected according to their effectiveness for the intended purpose and include, for example, methods using such techniques as gas chromatography (Chem. Pharm. Bull., 16:699–701, 1968), gas chromatography-mass spectrometry (Sci, 176: 177–180, 1972), high-performance liquid chromatography (Life Sci., 14:311–322, 1974) and the enzymeisotope method (Circ. Res., 26:53–57, 1970).

There has been little study, however, on the determination of the metabolites, and no suitable method for accurate and highly sensitive determination thereof has yet been established. Recent advancements in high-performance liquid chromatography have made it possible to separate the components of a substance which may contain the metabolites. Thus, as described in "J. Chromatogr., 116:240–243, 1976," the analysis of such a substance may be carried out using the most recent advancement in high-performance liquid chromatography in combination with spectrophotometry. However, when absorbance at 280 nm is used as described in the above-cited paper, a problem has been encountered in respect of the selectivity for quantifying the metabolites from biological samples composed of many components including mono-phenolic compounds which have maximum absorption around 280 nm. In addition, the described method is disadvantageous in that the sensitivity also is insufficient for quantifying extremely small amounts of the metabolites as in normal human urine.

It is described in "Nature, MacMillan Journals Limited (170:247–250, 1952)" that the solution of mixed ferric chloride and potassium ferricyanide was used as a color developer in paper chromatographic analysis of phenols. The reference only states that with such compounds the instaneous development of a color will be produced (refer to the 14th line from the bottom, left column, page 250). Thus, it has not been known that the reactivities therewith are different depending upon the types of phenols.

SUMMARY OF THE INVENTION

Under the circumstances, it is the principal object of the present invention to provide a method and apparatus for determining, with excellent selectivity and high sensitivity, catecholic compounds and their related compounds contained in a substance, particularly in a biological substance.

Other and further objects, features and advantages of the present invention will be more fully understood from the following description.

As the result of various studies by the inventors, it has now been found that, when ferric chloride and potassium ferricyanide are used as reaction reagents, there are differences between the reactivity of catecholic compounds as well as their metabolites and the reactivity of monophenolic compounds (interferers). That is to say, the reaction of dihydroxyphenyl compound (catecholic compounds such as catecholamines and their dihydroxyphenyl metabolites) and that of hydroxymethoxyphenyl compounds (metabolites of catecholic compounds) with the reagents have been found to occur faster than the reaction of monohydroxyphenyl compounds (the so-called monophenolic compounds) with the same reagents.

Thus, according to the present invention, there are provided a method and an apparatus, based on this new finding, to determine catecholic compounds and their metabolites contained in a substance which also may contain mono-phenolic compounds, by allowing the substance to react with ferric chloride and potassium ferricyanide as reagents and utilizing the differences in the reactivities of the components of the substance to the reagents.

DESCRIPTION OF THE PREFERRED EMBODIMENTS

Figure 1:
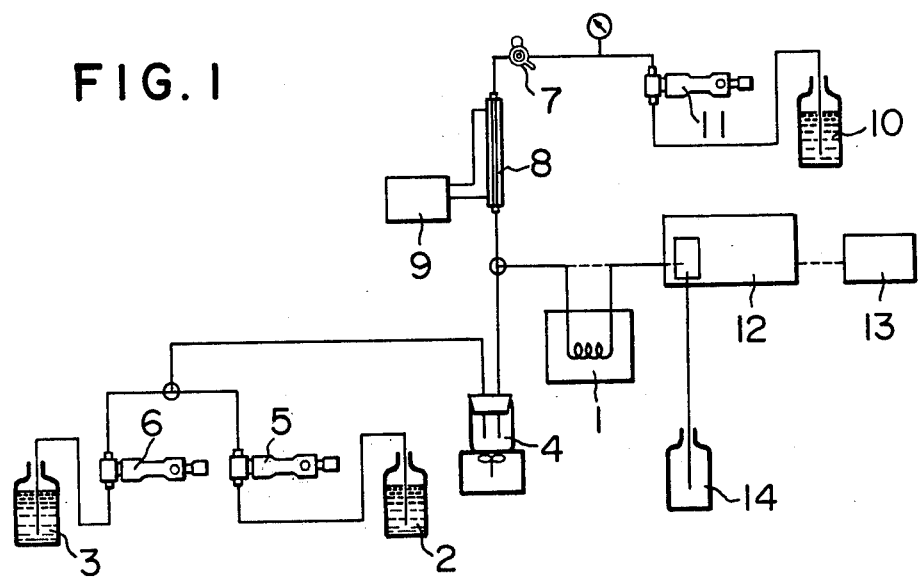
FIG. 1 is a diagram showing a preferred embodiment of the apparatus for practising the method of this invention.

The method of this invention is especially suitable for determining catecholic compounds present in the animal and vegetable kingdoms and others, particularly catecholamines such as dopamine, norepinephrine and epinephrine, and their metabolites including, for example, 3-methoxytyramine, normetanephrine, metanephrine, homovanillic acid, vanillylmandelic acid, 3,4-dihydroxyphenylacetic acid, 3,4-dihydroxymandelic acid, 3-methoxy-4-hydrophenylglycol and 3,4-dihydroxyphenylglycol.

According to the present invention, a substance or sample containing catecholic compounds and their related compounds is allowed to react with ferric chloride and potassium ferricyanide simultaneously or consecutively, in which ferric chloride and potassium ferricyanide are used as reaction reagents preferably in the form of aqueous solutions. Thus, though both the reagents may be dissolved in water and the resultant solution may be allowed to react with such a sample, it is usually preferable to separately prepare solutions of the respective reagents and mix the solutions just before the reaction with the two reagents takes place. Alternatively, the present invention can be carried out, after solutions of the respective reagents have been prepared, by allowing one of the reagents (one of the solutions) to react with a sample and then allowing the resultant product to react with the other reagent (the other solution).

The reaction with one of the reagents or with both the reagents is performed, preferably in the presence of a buffer such as citrate buffer solution, preferably in the acidic region a pH of below 6. It is also preferable to allow the reaction to occur at a temperature between 4° and 100° C.

While the proper concentrations of the solutions of the reagents depend on the concentration of the respective components in the sample to be determined, solutions of ferric chloride and potassium ferricyanide are prepared preferably in concentrations of 0.01 to 0.5 M and 0.01 to 0.5 M, respectively, for obtaining the specific reactivity and high sensitivity. While the specific reaction may occur in about one to several minutes, the suitable reaction time is from about 1.5 to 5 minutes.

According to a preferred embodiment of this invention, the overall reaction products are spectrophotometrically analyzed to determine each component contained in the sample. That is to say, as a bluish color will develop due to the reaction of the respective components with the reagents, each component can be selectively quantified by measuring its absorbance at 600 to 700 nm.

More specifically, the quantitative analysis may be carried out using a calibration standard prepared in advance for each of the components which may be contained in the sample. For example, when each component is allowed to react, with 0.03 M ferric chloride solution and 0.03 M potassium ferricyanide solution at a reaction temperature of 45° C. for a reaction time of 1.5 minutes, and its absorbance at 690 nm is monitored and recorded, the recorder response for each component is linear to the concentrations of each components, for example, 3,4-dihydroxymandelic acid, 3,4-dihydroxyphenylacetic acid, homovanillic acid, 3-methoxy-4-hydroxyphenylglycol, etc. in concentrations up to 400 ng, and thus, such linearity can be used as the calibration standard.

In addition, the method of this invention may be accomplished in combination with high-performance liquid chromatography. In such an embodiment, a sample is allowed to react with the reagents after separation of the components thereof by means of high-performance liquid chromatography, and then is analyzed spectrophotometrically to quantify each component. While the column-packing material for liquid chromatography may be properly selected from among commonly available packing materials, such as ion-exchange resins, resins of normal phase and resins of reversed phase, for a specific sample, such as column-packing material as Spherisorb S5 ODS (available from Phase Separations Ltd.) may be preferred. This embodiment is especially suitable for quantifying catecholamines and their metabolites contained in plant and biological substances, particularly in urine, with selectivity and high sensitivity.

This invention also provides a determination apparatus for practising the above-described method. The determination apparatus of this invention comprises a reaction vessel in which a substance containing catecholic compounds and their metabolites is allowed to react with ferric chloride and potassium ferricyanide as reagents and a spectrophotometer in connection with the reaction vessel. A spectrophotometer of the type commonly available on market may be used.

The reaction vessel is connected, preferably with a device to deliver a substance or sample containing catecholic compounds and their metabolites and a device to deliver the reagents. As the device for delivering a sample, a commonly available sample injector may be used. The device for delivering the reagents is preferably provided with a reservoir for ferric chloride and a reservoir for potassium ferricyanide. Though the reagents may respectively be delivered directly to the reaction vessel, it is especially preferable to install a mixing vessel between and connected with these reagent reservoirs and the reaction vessel so that a mixture of the two reagents can be delivered to the reaction vessel.

The reagents can be delivered by a pump. In addition, it is preferable to install a buffer solution reservoir prior to the sample injector, to deliver the buffer solution to the injector via the pump and to deliver the sample to the reaction vessel.

It is further preferable for the determination by this invention to install a high-performance liquid chromatograph between the sample delivery device and the reaction vessel and to connect it with them. The high-performance liquid chromatograph may be of a commonly available type, comprising a column packed with a commonly available packing material and a liquid circulation bath by which liquid, preferably water, at a constant temperature is circulated for the column.

A preferred arrangement of the determination apparatus of this invention is illustrated in FIG. 1. In this figure, a reaction vessel 1, a ferric chloride reservoir 2 and a potassium ferricyanide reservoir 3 are connected with each other through a mixing vessel 4, and the solutions of the reagents are delivered by pumps 5 and 6 respectively. The mixing of the reagents can be made by an optional means, such as a magnetic stirrer. A sample is injected from a sample injector 7 and delivered to the reaction vessel 1. In case of using a high-performance liquid chromatograph, the sample injected from the injector 7 is delivered to the reaction vessel 1 through the column of the high-performance liquid chromatograph 8. The numeral 9 represents a constant temperature water circulation bath for the column 8. A buffer solution reservoir 10 is installed, preferably prior to the sample injector 7, and the buffer solution is delivered to the sample injector 7 by a pump 11. Next to the reaction vessel 1, a commonly available spectrophotometer 12 is connected, and the result of the absorption is recorded by a recorder 13. The reaction mixture after completion of the determination is drained into a waste reservoir 14.

According to this invention, determination of each component of catecholic compounds (especially catecholamines) and their metabolites in a substance can be made selectively with high sensitivity by a simple and economical means, preferably in combination with a high-performance liquid chromatograph, and this invention is highly useful for analysis, quantifying, or diagnosis in the fields of medicine, pharmacy, biochemistry, pharmacology and neurochemistry.

Below are described experiments conducted for elucidating that catecholic compounds and their related compounds (their metabolites) can be determined according to the present invention.

In all the experiments, determination was performed with equipment the same as that illustrated in FIG. 1, with the exception that the column 8 for high-performance liquid chromatograph and the constant temperature water circulation bath 9 were excluded. As samples, the following compounds were used all in a concentration of $2 \times 10^{-9}$ M:

3,4-dihydroxymandelic acid (DOMA)
homovanillic acid (HVA)
3,4-dihydroxyphenylacetic acid (DOPAC)
vanillylmandelic acid (VMA)
3-methoxy-4-hydroxyphenylglycol (MHPG)
dopa (DOPA)
dopamine (DA)
norepinephrine (NE)
epinephrine (E).

In addition, for examining the behavior of monohydroxyphenyl compounds as interfering compounds, two samples were also prepared containing 4-hydroxyphenylacetic acid and 3-hydroxyphenylacetic acid, respectively, both in a concentration of $2 \times 10^{-9}$ M, that is, the same concentration as the foregoing samples.

Aqueous solutions of ferric chloride and potassium ferricyanide each in a desired concentation were delivered by pumps respectively from the ferric chloride reservoir 2 and the potassium ferricyanide reservoir 3 to the mixing vessel 4, and then to the reaction vessel 1, and each sample was delivered to the reaction vessel 1 from the sample injector 7. The reaction was allowed to take place at 45° C. for a desired period of time, and then the absorbance was monitored with the spectrophotometer 12.

Figure 2:
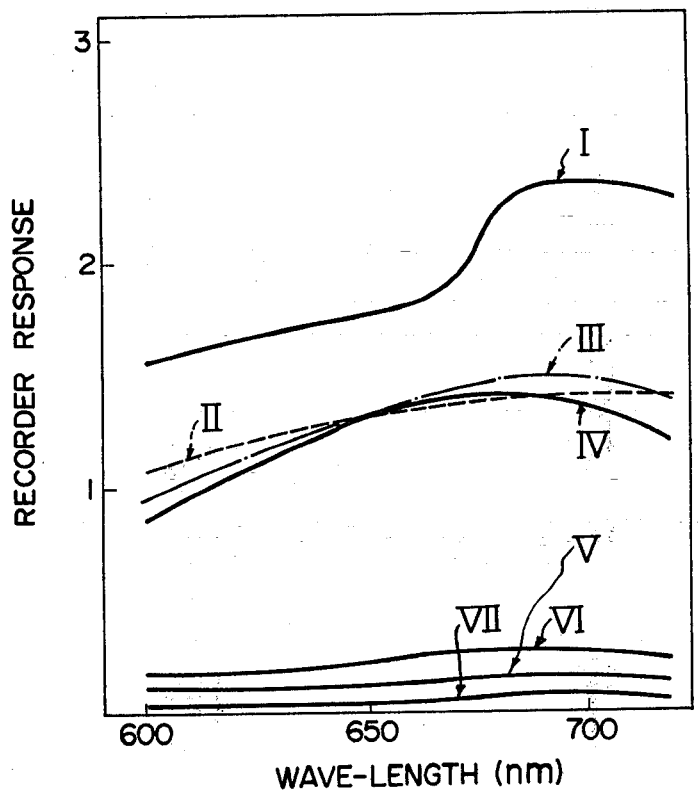
FIGS. 2 through 6 are graphic presentations to indicate the specificity and sensitivity of catecholic compounds and hydroxymethoxy compounds to the reagents.

(A) Reactivity and sensitivity of each sample:

With the reaction reagents in the concentration of 0.02 M ferric chloride and 0.01 M potassium ferricyanide, each sample was allowed to react for a reaction time of 1.5 minutes, and the absorbance of each sample was monitored at wavelengths between 600 and 720 nm, the results of which are shown in FIG. 2.

In FIG. 2, the absorbance of each sample is represented by a Roman numeral as follows:

I=DOMA; II=HVA; III=DOPAC; IV=VMA;
V=4-dihydroxyphenylacetic acid; VI=MHPG;
VII=3-hydroxyphenylacetic acid.

As mentioned earlier, the concentrations of V and VII are 10 times higher than that of the others.

As clarified from the results, dihydroxyphenyl compounds (catecholic compounds) and hydroxymethoxyphenyl compounds exhibited higher sensitivity than monohydroxyphenyl compound. For example, from the absorbances at 690 nm, the former group of compounds was found to be several times higher in sensitivity than the latter group of compounds in the spectrometric determination.

Figure 3:
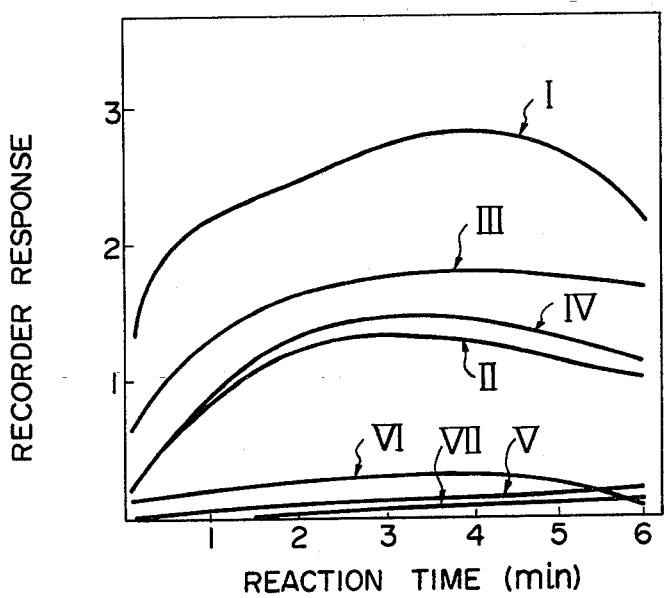

(B) Reaction time:

With the reagents in the concentrations of 0.02 M ferric chloride and 0.01 M potassium ferricyanide, the reaction was allowed to proceed for different reaction times, and the respective absorbances were monitored at the wavelength of 690 nm, the results of which are shown in FIG. 3. The Roman numerals in the figure have the same meanings as in FIG. 2.

In order to increase the selectivity of dihydroxyphenyl compounds and hydroxymethoxyphenyl compounds over monohydroxyphenyl compounds at the present concentrations of the reagents, it was found preferable to allow the reaction to proceed for about 1.5 minutes.

Figure 4:
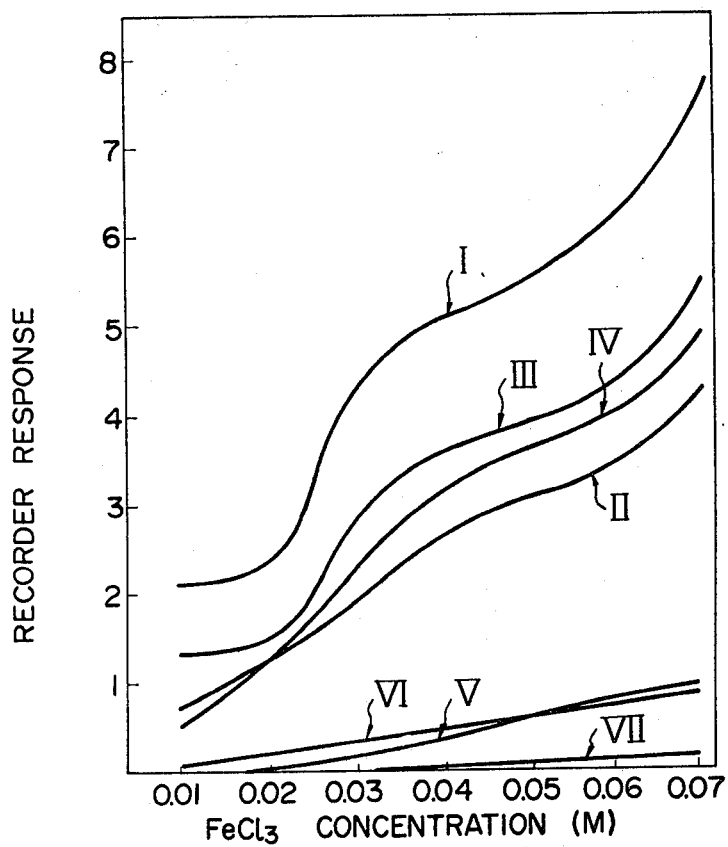
Figure 5:
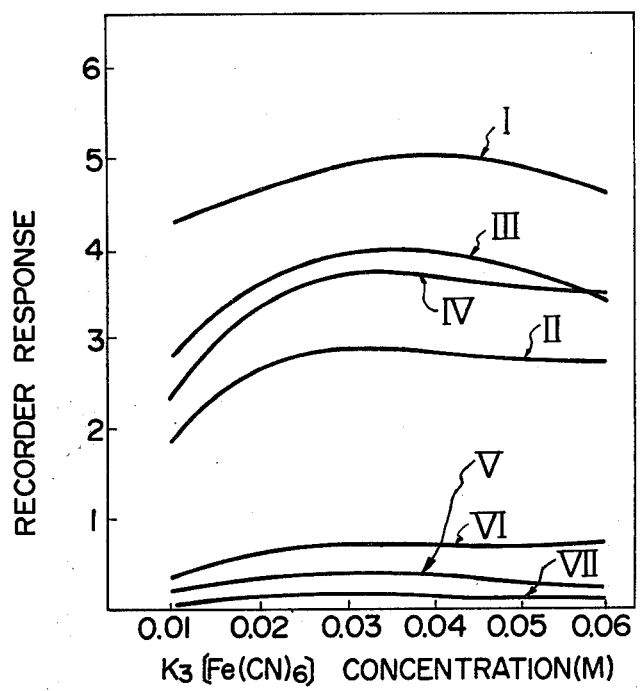

(C) Concentrations of ferric chloride solution and potassium ferricyanide solution:

FIG. 4 represents the results of determination of absorbance at the wavelength of 690 nm after the reaction was allowed to proceed for 1.5 minutes with ferric chloride solution in the fixed concentration of 0.01 M and potassium ferricyanide solution in various concentrations. Similarly, the absorbance, using ferric chloride solution in the fixed concentrations of 0.03 M and potassium ferricyanide solution in various concentrations, is depicted in FIG. 5. The Roman numerals in FIGS. 4 and 5 have the same meanings as in FIG. 2.

From these results, the optimal concentration of each reaction reagent was found at 0.02 to 0.03 M ferric chloride and at 0.02 to 0.04 M for potassium ferricyanide. In addition, in the reaction with 0.03 M ferric chloride solution and 0.03 M potassium ferricyanide solution, about 30 times higher sensitivity for dihydroxyphenyl compounds and about 20 times higher sensitivity for hydroxymethoxy compounds were obtained as compared wih monohydroxy compounds (FIG. 5).

Figure 6:
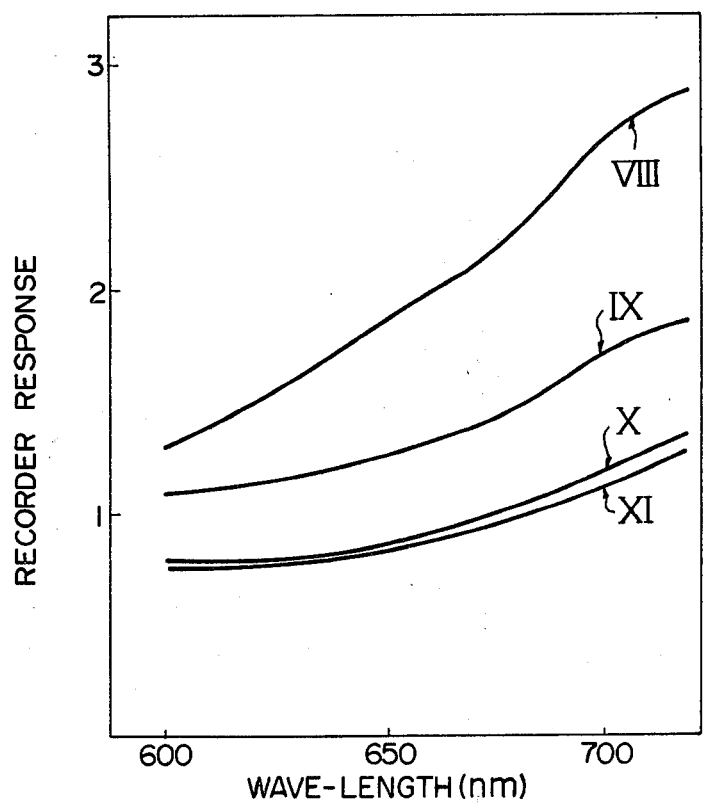

(D) Determination of catecholamines was performed under the same conditions as described in Experiment A, the results of which are shown in FIG. 6. The chromatograms in the figure show the absorbances designated as VIII for DOPA, as IX for epinephrine, as X for norepinephrine and as XI for dopamine.

As clarified from the results, catecholamines can also be determined with high sensitivity.

EXAMPLE 1

Determination of a sample containing catecholic compounds and their metabolites was performed using an apparatus which, similar to that shown in FIG. 1, was equipped with a high-performance liquid chromatograph, with the modification as specified below so as to permit a comparison of the data obtained by the method of the present invention with those by the conventional method.

Instead of connecting with the reaction vessel 1, the column 8 was connected with another spectrophotometer, with which the absorbance of the column eluate was monitored at a wavelength of 280 nm according to the conventional method. The column eluate, the absorbance of which has been determined at 280 nm, was delivered to the reaction vessel 1 for the reaction with the reagents, and then its absorbance at the wavelength of 690 nm was monitored with the spectrophotometer 12.

As a sample, a mixture of 400 ng each of 3,4-dihydroxymandelic acid (DOMA), a vanillylmandelic acid (VMA), 3-methoxy-4-hydroxyphenylglycol (MHPG), 3,4-dihydroxyphenylacetic acid (DOPAC) and homovanillic acid (HVA) was used.

The conditions for the determination were as follows:
Size of Column: 4.6 mm in inside diameter and 25 cm in length.
Packing Material: Spherisob S5 ODS.
Column Temperature: 45° C.
Mobile Phase: 10% methanol in 0.1 M citrate buffer solution (pH 3.4).
Flow Rate of Mobile Phase: 0.6 ml per minute.
Concentration of Reagents: 0.06 M ferric chloride solution; and 0.06 M potassium ferricyanide solution.

Flow Rates of Reagents: 0.3 ml per minute, respectively.

Detection:
 280 nm, 1.0 AUFS (the conventional method)
 690 nm, 1.28 AUFS (the method of this invention).

Figure 7:
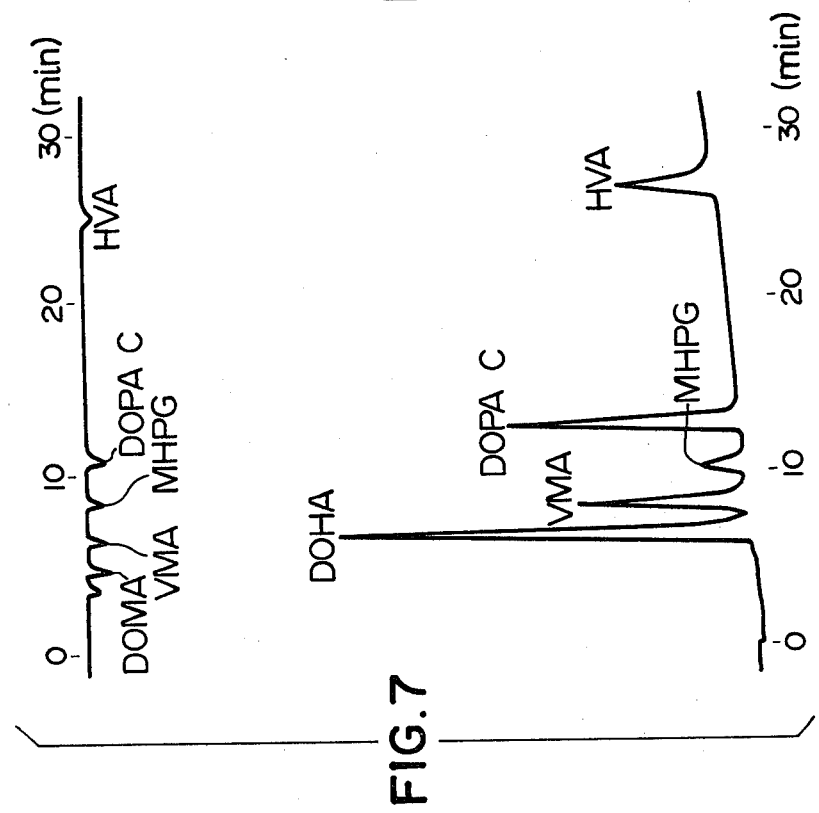

The results of the determination are illustrated in FIG. 7. The upper chromatogram in the figure was obtained by monitoring the absorbance of 280 nm according to the conventional method, and the lower chromatogram was obtained by monitoring the absorbance at 690 nm according to the method of this invention, and the abbreviations at the peaks of the chromatograms represent the components as stated above.

As can be seen from these results, each component can be quantified with high sensitivity by the method of this invention.

EXAMPLE 2

Metabolites of catecholamines contained in urine were determined, using the same modified equipment and under the same conditions for the determination as in Example 1, except that the detection conditions were as stated below.

Detection:
 280 nm, 0.1 AUFS (the conventional method)
 690 nm, 0.64 AUFS (the method of this invention).

Figure 8:
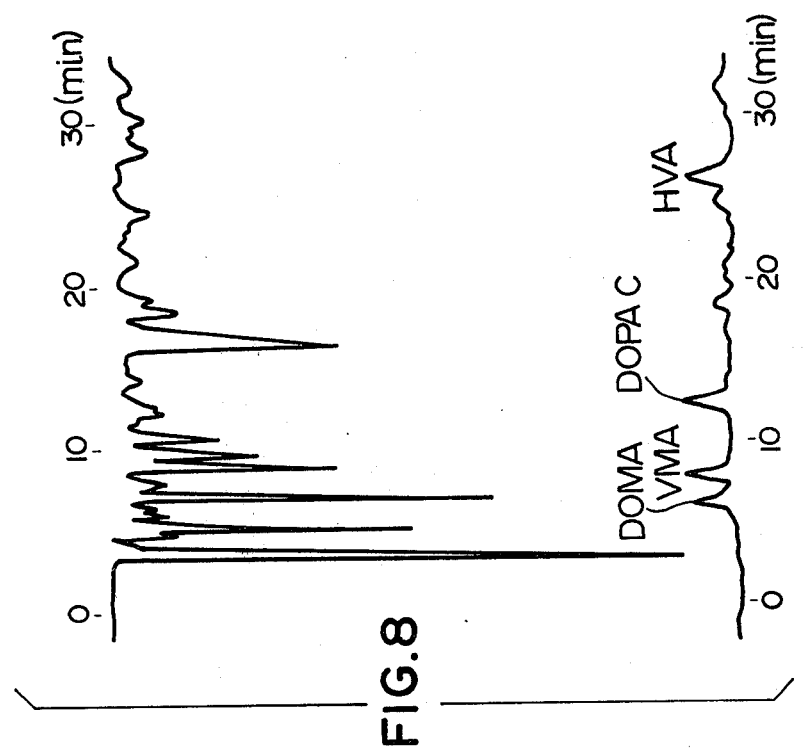
FIGS. 7 and 8 are graphic presentations representing the results obtained from the determination of standard samples and urine, respectively.

A 5 ml of urine was collected in a separatory funnel, to which 0.5 ml sample of 1 N hydrochloric acid and 1.5 g of sodium chloride were added. The mixture was agitated and 20 ml of ethyl acetate was added and shaken therewith. The ethyl acetate layer was collected, and evaporated at 40° C. under reduced pressure to dryness, and the residue was dissolved in 2 ml of 0.2 N acetic acid. An aliquot of the resultant solution was injected into the column 8 through the injector 7. FIG. 8 is one of the results obtained according to the procedure. The abbreviations of the respective components as well as the upper and lower chromatograms have the same meanings as in FIG. 7. As clarified from these results, considerably complicated chromatograms are obtained by the conventional method, and so it is difficult to quantify each component selectively. By contrast, simple and clear peaks of the components to be determined are obtained by the method of this invention, greatly facilitating selective quantifying.

What is claimed is:

1. A method of determining selectively catecholic compounds and their related compounds contained in a substance which also contains mono-phenolic compounds, comprising reacting said substance simultaneously or consecutively with solutions of ferric chloride and potassium ferricyanide as reaction reagents for such a reaction period and in such concentrations of the solutions of the reaction reagents that the reaction products of the catecholic compounds or their related compounds with the reaction reagents will exhibit absorbances sufficiently higher than the reaction products of the monophenolic compounds when analyzed by spectrophotometry at the wavelength of 600 to 700 nm to enable selective determination of the catecholic compounds and their related compounds in the presence of the mono-phenolic compounds, and analyzing, after the reaction is completed, the reaction products by spectrophotometry at the wavelength of 600 to 700 nm so as to determine the catecholic compounds and their related compounds.

2. The method as claimed in claim 1, in which, said reaction is conducted for a reaction period of from about 1.5 to 5 minutes and in the concentrations of the solutions of ferric chloride and potassium ferricyanide of 0.01 to 0.5 M and 0.01 to 0.5 M, respectively.

3. The method as claimed in claim 1, in which, prior to the reaction, catecholic compounds, their related compounds and mono-phenolic compounds contained in the substance are separated from other compounds in said substance by means of high-performance liquid chromatography.

* * * * *